(12) United States Patent
Gulati

(10) Patent No.: US 7,351,692 B2
(45) Date of Patent: Apr. 1, 2008

(54) METHOD AND COMPOSITION FOR POTENTIATING THE ANTIPYRETIC ACTION OF A NONOPIOID ANALGESIC

(75) Inventor: Anil Gulati, Naperville, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 485 days.

(21) Appl. No.: 10/459,905

(22) Filed: Jun. 12, 2003

(65) Prior Publication Data

US 2003/0236235 A1   Dec. 25, 2003

Related U.S. Application Data

(60) Provisional application No. 60/390,045, filed on Jun. 19, 2002.

(51) Int. Cl.
*A61K 38/00*   (2006.01)
*A61K 31/16*   (2006.01)

(52) U.S. Cl. .......................................... 514/11; 514/629

(58) Field of Classification Search .................. 514/11, 514/629
See application file for complete search history.

(56) References Cited

U.S. PATENT DOCUMENTS

| | | |
|---|---|---|
| 5,612,359 A | 3/1997 | Murugesan |
| 5,811,416 A | 9/1998 | Chwalisz et al. |
| 2002/0082285 A1 | 6/2002 | Lebwohl |

FOREIGN PATENT DOCUMENTS

| | | |
|---|---|---|
| EP | 0-815 870 | 1/1998 |
| WO | WO 96/19233 | 6/1996 |
| WO | WO 01/91734 | 12/2001 |
| WO | WO 03/009805 | 2/2003 |
| WO | WO 03/045434 | 6/2003 |

OTHER PUBLICATIONS

Remington's Pharmaceutical Sciences, 1985, 17th Edition, p. 1099-1102, 1107, 1110-1112).*
K. Matsumaru et al., *J. Gastroenterol*, 32, 164-170 (1997).
A.E. Duggan et al., *Aliment Pharmacol Ther*, 13, 631-635 (1999).
A.S.C. Fabricio et al., *British Journal of Pharmacology*, 125, 542-548 (1998).
S. Bhalla et al., *Peptides*, 23, 1837-1845 (2002).
H.N. Bhargava et al., *The Journal of Pharmacology and Experimental Therapeutics*, vol. 252, No. 3, 901-907 (1990).
C. Wu, *Exp. Opin. Ther. Patents*, 10 (11), 1653-1668 (2000).
M.F. Jarvis et al., *European Journal of Pharamcology*, 388, 29-35 (2000).
G. Davar et al., *NeuroReport*, 9, 2279-2283 (1998).

* cited by examiner

*Primary Examiner*—Sreeni Padmanabhan
*Assistant Examiner*—Layla Soroush
(74) *Attorney, Agent, or Firm*—Marshall, Gerstein & Borun LLP

(57) ABSTRACT

A composition and method of treating fever, and optionally treating pain, is disclosed. The composition and method utilize a nonopioid analgesic and an endothelin antagonist as active agents to treat fever in mammals, including humans. The composition also is useful in the prevention and treatment of stroke and other cardiovascular disorders, like myocardial infarction.

11 Claims, 5 Drawing Sheets

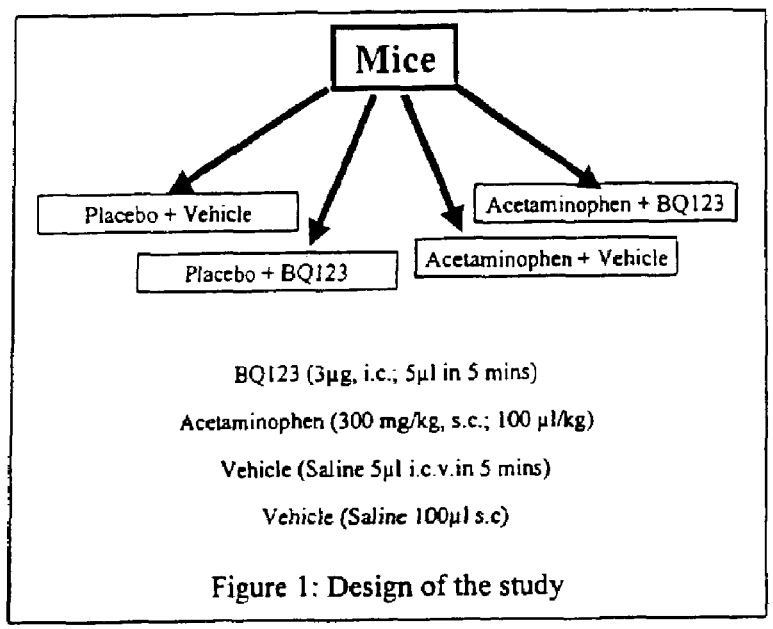
Figure 1: Design of the study
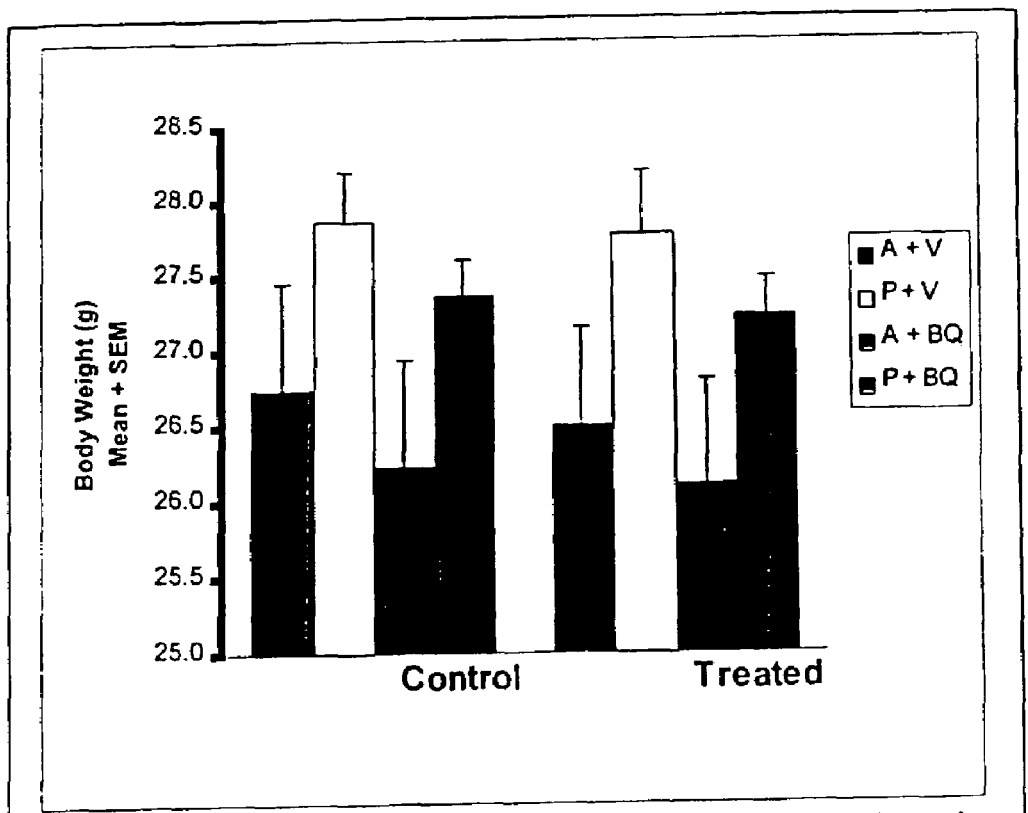
Figure 2: Effect of BQ123 pretreatment on acetaminophen induced change in body weight. No difference in change in body weight was observed between any groups.

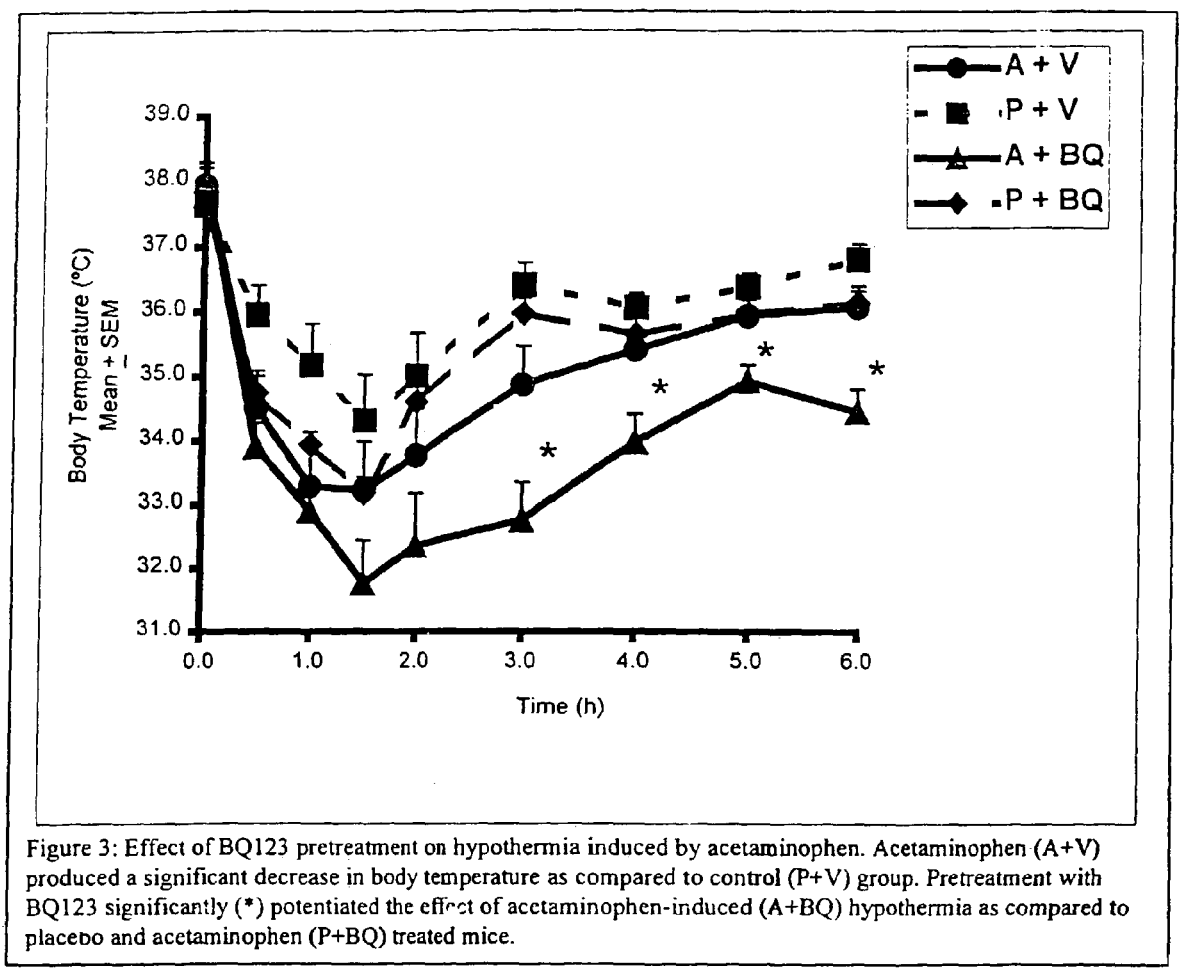
Figure 3: Effect of BQ123 pretreatment on hypothermia induced by acetaminophen. Acetaminophen (A+V) produced a significant decrease in body temperature as compared to control (P+V) group. Pretreatment with BQ123 significantly (*) potentiated the effect of acetaminophen-induced (A+BQ) hypothermia as compared to placebo and acetaminophen (P+BQ) treated mice.

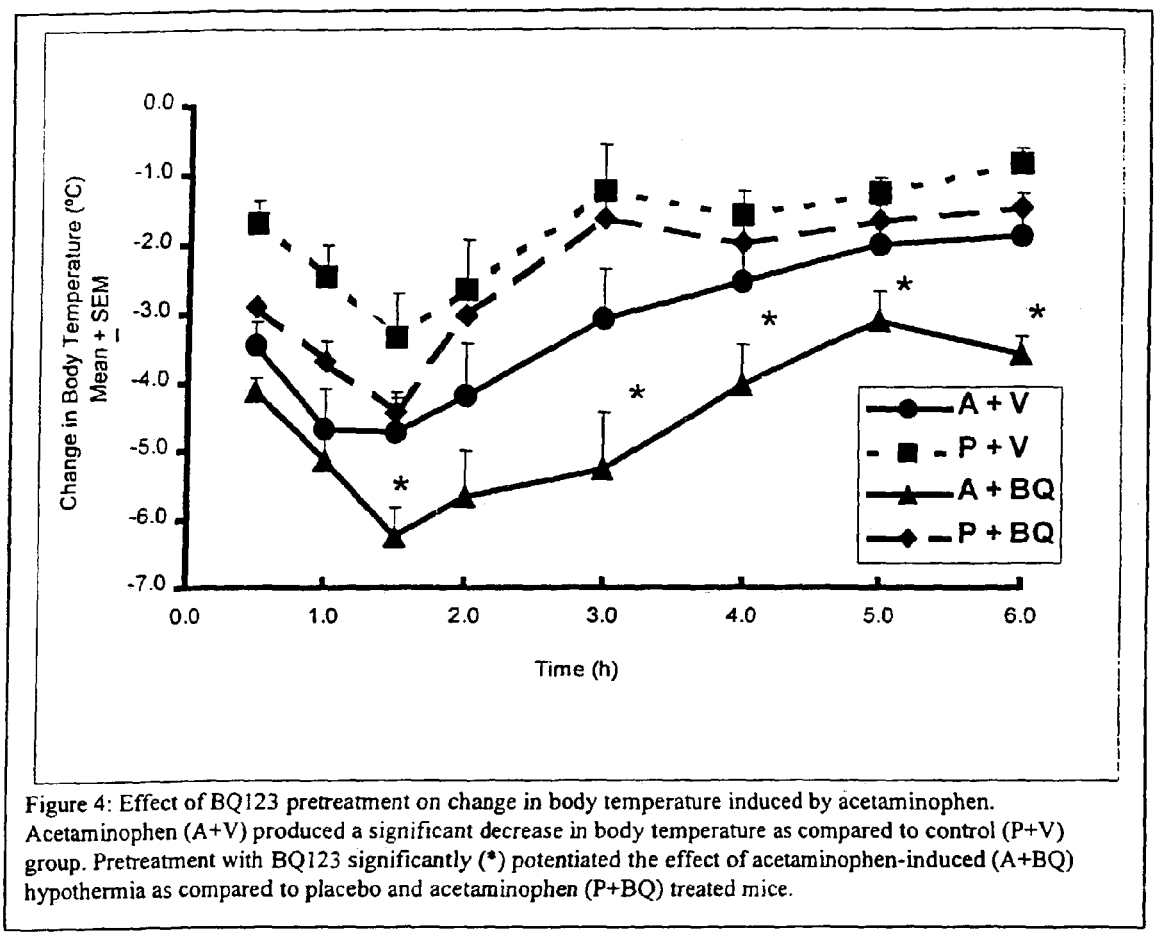

Figure 4: Effect of BQ123 pretreatment on change in body temperature induced by acetaminophen. Acetaminophen (A+V) produced a significant decrease in body temperature as compared to control (P+V) group. Pretreatment with BQ123 significantly (*) potentiated the effect of acetaminophen-induced (A+BQ) hypothermia as compared to placebo and acetaminophen (P+BQ) treated mice.

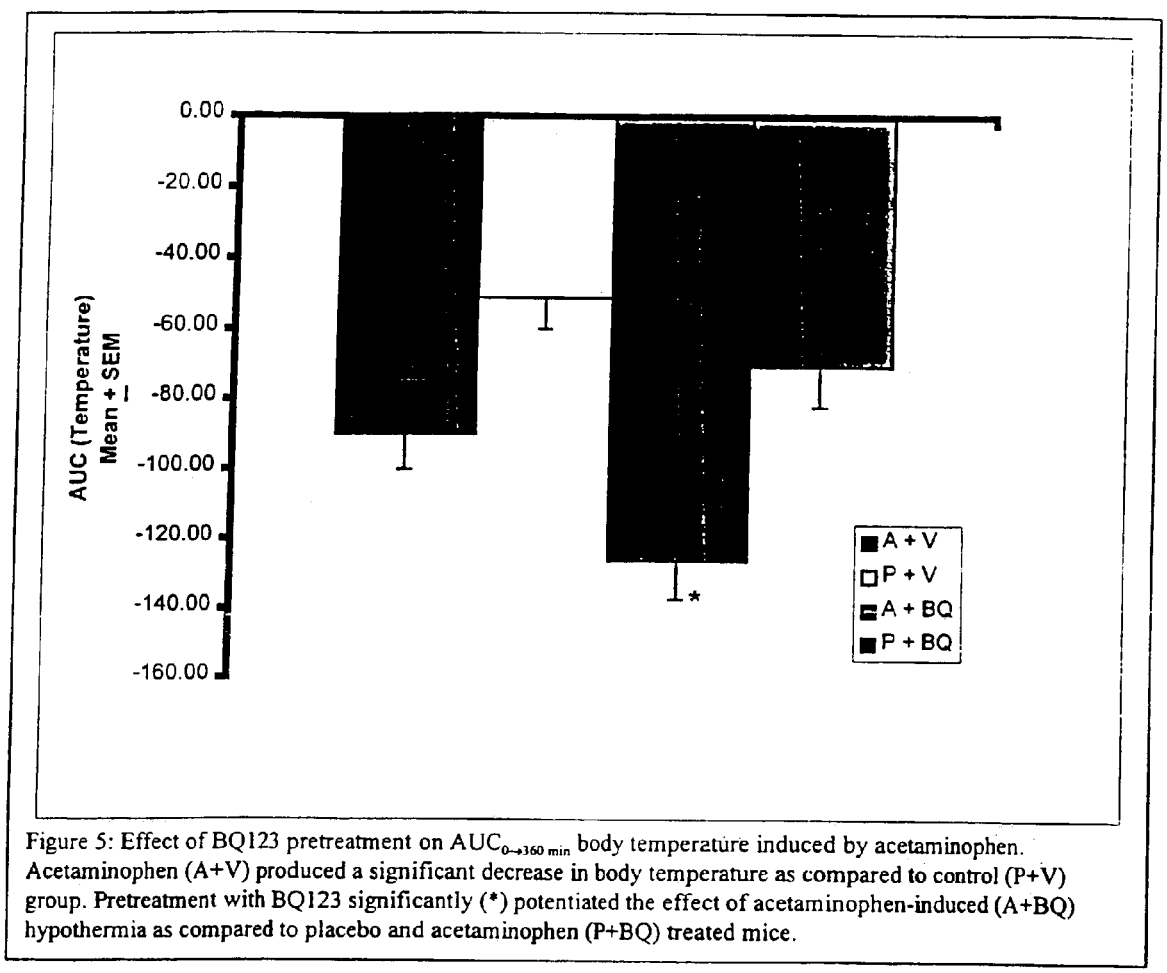

Figure 5: Effect of BQ123 pretreatment on $AUC_{0 \to 360\,min}$ body temperature induced by acetaminophen. Acetaminophen (A+V) produced a significant decrease in body temperature as compared to control (P+V) group. Pretreatment with BQ123 significantly (*) potentiated the effect of acetaminophen-induced (A+BQ) hypothermia as compared to placebo and acetaminophen (P+BQ) treated mice.

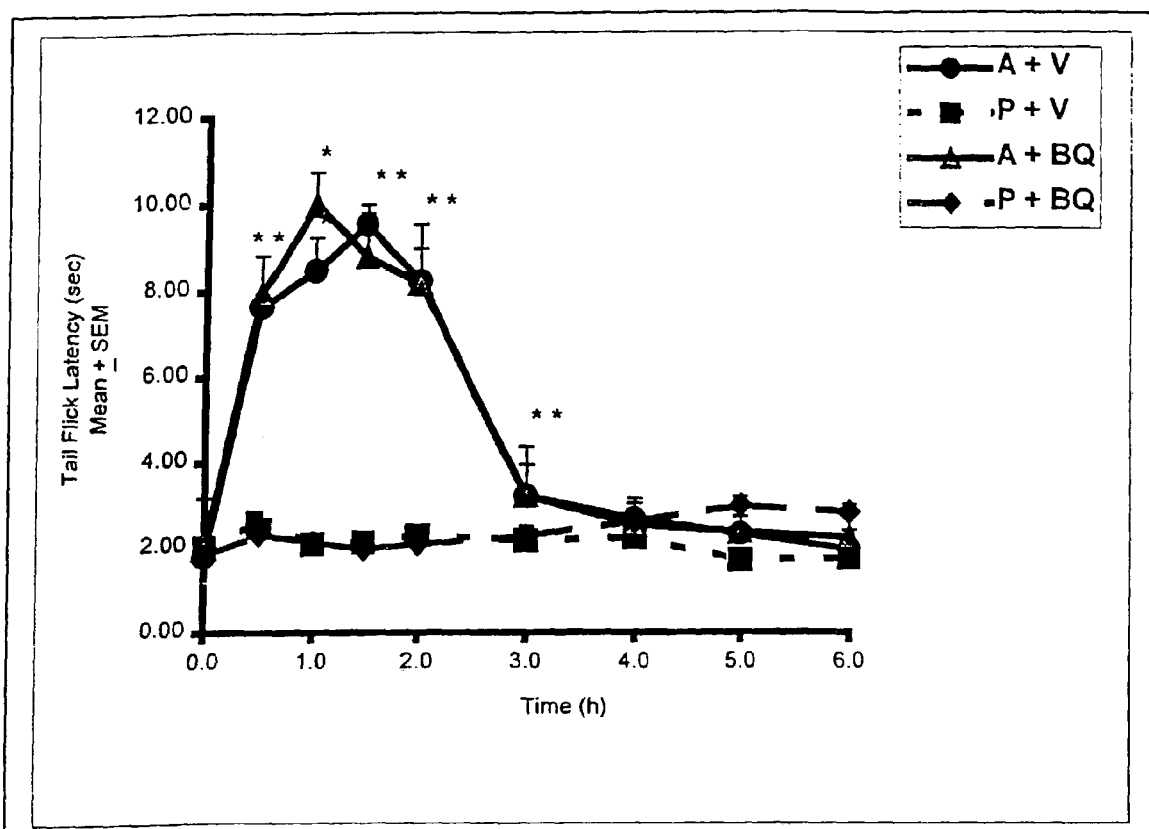
Figure 6: Effect of BQ123 pretreatment on analgesia induced by acetaminophen. Acetaminophen (A+V) produced a significant increase in tail flick latency as compared to control (P+V) group. Pretreatment with BQ123 did not affect acetaminophen-induced (A+BQ) tail flick latency as compared to placebo and acetaminophen (P+BQ) treated mice.

METHOD AND COMPOSITION FOR POTENTIATING THE ANTIPYRETIC ACTION OF A NONOPIOID ANALGESIC

CROSS REFERENCE TO RELATED APPLICATIONS

This application claims the benefit of U.S. provisional patent application Serial No. 60/390,045, filed Jun. 19, 2002.

FIELD OF THE INVENTION

The present invention relates to the treatment of fever using a nonopioid analgesic and an endothelin antagonist. More particularly, the present invention relates to a method of potentiating the antipyretic action of a nonopioid analgesic, like acetaminophen, in a mammal by administration of a therapeutically effective amount of an endothelin antagonist. The composition and method potentiate the antipyretic action of the nonopioid analgesic, without adversely effecting the analgesic action of the nonopioid analgesic.

BACKGROUND OF THE INVENTION

Fever is one of the most common conditions requiring an individual to seek medical attention. In addition to treating the cause of the fever, medical personnel treat, i.e., reduce, the fever itself using analgesics, antipyretics, and/or physical cooling methods.

The nonopioid analgesic and antipyretic drugs are a small, heterogeneous group of compounds which, unlike opioid analgesics, are free of significant addiction liability. Most of these nonopioid analgesic/antipyretic drugs affect both pain and fever. Consequently, they are widely used for minor aches and pains, headaches, and the general feeling of malaise that accompanies febrile illnesses, and to alleviate symptoms of rheumatic fever, arthritis, gout, and other musculoskeletal diseases and conditions.

The salicylate group of analgesics and antipyretics are by far the most commonly used. This group of drugs is consumed at a rate of more than 10,000 tons annually. In addition, paracetamol (i.e., acetaminophen) is one of the most widely used of all drugs, with a wealth of experience clearly establishing it as the standard antipyretic and analgesic for mild to moderate pain states. First used clinically by von Mering in 1893, acetaminophen was not used commercially in the United States until 1950. During the 1960s and 1970s, investigators voiced concerns about the toxicity of nonprescription analgesics, but in normal use, acetaminophen exhibited a consistent safety profile. Currently, acetaminophen is a first-line choice for pain management and antipyresis in a variety of patients, especially patients susceptible to the adverse effects of salicylates, including children, pregnant women, the elderly, individuals with osteoarthritis, and individuals with noninflammatory musculoskeletal conditions. See L. F. Prescott, *Am. J. Ther.*, 7(2), pp. 143-147 (2000).

Acetaminophen is metabolized primarily in the liver, and the metabolites generally exhibit no harmful effects. The mechanism of action of acetaminophen has not been satisfactorily explained. Acetaminophen inhibits both COX-1 and COX-2 weakly in vitro, and reduces prostaglandin synthesis markedly in vivo. Evidence is accumulating for the existence of a COX-2 variant or a new COX enzyme that can be inhibited by acetaminophen (R. Botting, *J. Physiol, Pharmacol.*, 54 (4 Pt. 1), pp. 609-698 (2000)). COX-2-selective drugs, or null mutation of the COX-2 gene, reduce or prevent fever. Acetaminophen is an antipyretic and analgesic, but it lacks the antiinflammatory and anticoagulatory properties of other nonsteroidal antiinflammatory drugs (NSAIDs). This has led to a theory that a COX variant capable of inhibition by acetaminophen exists. Inhibition of pharmacologically distinct COX-2 enzyme activity by acetaminophen, therefore, has been theorized as the mechanism of action of this important antipyretic drug (D. L. Simmons et al., *Clin. Infect. Dis.*, 31 *Supp.* 5, pp. 5211-5218 (2000)).

The present invention is directed to the discovery that the antipyretic action of a nonopioid analgesic can be modified by coadministration of an endothelin receptor antagonist, hereafter termed an "endothelin antagonist."

SUMMARY OF THE INVENTION

The present invention is directed to administration of an endothelin antagonist in combination with a nonopioid analgesic to potentiate the antipyretic action of the nonopioid analgesic without adversely affecting the analgesic properties of the analgesic. In addition, administration of a nonopioid analgesic in combination with an endothelin antagonist significantly potentiates the antipyretic action of the nonopioid analgesic at a dose of analgesic used-to provide a pain-reducing effect. The significant reduction in fever provided by the composition and method of the present invention reduces or eliminates various adverse effects associated with fever.

Accordingly, one aspect of the present invention is to provide a composition comprising a nonopioid analgesic, e.g., acetaminophen, and an endothelin antagonist that provides an enhanced antipyretic action and also treats pain. A present composition provides an improved antipyretic action without adversely affecting the analgesic properties of the nonopioid analgesic.

The present invention, therefore, provides a composition and method of improving antipyretic action of a nonopioid analgesic. In particular, the present invention is directed to compositions containing a nonopioid analgesic and an endothelin antagonist, and to methods of using the composition to significantly reduce fever and treat pain. More particularly, the present invention is directed to compositions containing acetaminophen and an endothelin antagonist, and to use of a nonopioid analgesic and endothelin antagonist, administered simultaneously or sequentially, in methods of reducing fever and treating pain.

An important aspect of the present invention, therefore, is to provide a method and composition for reducing fever, while maintaining the analgesic effect associated with a nonopioid analgesic.

Another aspect of the present invention provides an article of manufacture for human pharmaceutical use, comprising (a) a package insert, (b) a container, and either (c1) a packaged composition comprising a nonopioid analgesic and an endothelin antagonist or (c2) a packaged composition comprising a nonopioid analgesic and a packaged composition comprising an endothelin antagonist.

These and other aspects of the present invention will become apparent from the following detailed description of the preferred embodiments.

BRIEF DESCRIPTION OF THE DRAWINGS

FIG. 1 illustrates the groups of rats treated with a vehicle, endothelin antagonist, acetaminophen, and endothelin antagonist plus acetaminophen;

FIG. 2 contains bar graphs showing the effect of BQ123 pretreatment on acetaminophen-induced change in body weight;

FIG. 3 contains plots showing the effect of BQ123 pretreatment on hypothermia induced by acetaminophen;

FIG. 4 contains plots showing the effect of BQ123 pretreatment on change in body temperature induced by acetaminophen;

FIG. 5 contains plots showing the effect of BQ123 pretreatment on $AUC_{0-360\ min}$ body temperature induced by acetaminophen; and FIG. 6 contains plots showing the effect of BQ123 pretreatment on analgesia induced by acetaminophen.

DETAILED DESCRIPTION OF THE PREFERRED EMBODIMENTS

The present invention is directed to the simultaneous or sequential administration of a nonopioid analgesic and an endothelin antagonist to potentiate the antipyretic action of the nonopioid analgesic and to treat pain. In particular, the administration of a nonopioid analgesic and an endothelin antagonist potentiates the antipyretic action of the nonopioid analgesic, without adversely affecting the analgesic properties of the analgesic.

The present invention, therefore, provides compositions and methods of potentiating the antipyretic action of a nonopioid analgesic, while maintaining analgesic action. The present invention also provides pharmaceutical compositions comprising a nonopioid analgesic and an endothelin antagonist. Further provided are articles of manufacture comprising a nonopioid analgesic and an endothelin antagonist, packaged separately or together, and an insert having instructions for using these active agents.

The methods described herein benefit from the use of a nonopioid analgesic and an endothelin antagonist in the treatment and management of fever and pain. The nonopioid analgesic and endothelin antagonist can be administered simultaneously or sequentially to achieve the desired effect. The nonopioid analgesic and endothelin antagonist exert a substantial antipyretic action that is independent from the underlying disease or condition causing the fever.

For the purposes of the invention disclosed herein, the term "treatment" includes preventing, lowering, or eliminating fever and pain. As such, the term "treatment" includes both medical therapeutic and/or prophylactic administration, as appropriate.

The term "container" means any receptacle and closure therefor suitable for storing, shipping, dispensing, and/or handling a pharmaceutical product.

The term "insert" means information accompanying a product that provides a description of how to administer the product, along with the safety and efficacy data required to allow the physician, pharmacist, and patient to make an informed decision regarding use of the product. The package insert generally is regarded as the "label" for a pharmaceutical product.

The term "prodrug" means compounds that transform rapidly in vivo to a compound useful in the invention, for example, by hydrolysis. A thorough discussion is provided in Higuchi et al., *Prodrugs as Novel Delivery Systems*, Vol. 14, of the A.C.S.D. Symposium Series, and in Roche (ed.), *Bioreversible Carriers in Drug Design*, American Pharmaceutical Association and Pergamon Press, 1987.

Endothelin in the Central Nervous System

Endothelin (ET) is an extremely potent endothelium derived vasoconstriction factor (Hickey et al., 1985) that was isolated, sequenced, and cloned (Yanagisawa et al., 1988). Endothelins are 21 amino acid, highly potent vasoconstrictive peptides with two disulfide bonds. Endothelins are produced biologically by enzymatically cleaving preproendothelin to proendothelin, then to endothelin by endothelin-converting enzymes. ET exerts biological effects by binding to cell surface receptors which are 7-transmembrane receptors coupled to G-proteins. There are two distinct types of endothelin receptors, (a) the ET-1 selective $ET_A$ receptors primarily found on vascular smooth muscle and responsible for vasoconstriction, and (b) nonselective $ET_B$ receptors primarily found in vascular endothelium and responsible for vasodilation.

The vasoconstrictive effects of ET-1 are mediated predominantly by G-protein coupled $ET_A$ receptors (Reynolds et al., 1989). ET-1 also is made in high concentrations by prostate, metastatic cancers, and CNS. ET in the CNS is produced by endothelial cells and nonendothelial cells, such as neurons, astrocytes, and glial cells (MacCumber et al., 1990).

The global distribution of ET and its binding sites in the brain suggests that, in addition to being a vasoconstrictor, ET may be acting as an important neuropeptide in the CNS (Gulati et al., 1992). Endothelin (ET) receptor antagonists, in particular selective $ET_A$ or balanced antagonists $ET_A/ET_B$, represent a therapeutic area for diseases such as congestive heart failure (CHF) and pulmonary hypertension. BQ-123 and BMS-182874 are specific antagonists of $ET_A$ receptors (Ihara et al., 1992; Stein et al., 1994). Endothelin antagonists have profound effects on the pulmonary vasculature and the right heart, whereas ACE inhibitors primarily affect the peripheral vessel and the left heart.

Several studies indicate that the central ET receptors are predominantly of $ET_B$ subtype (Matsumura et al., 1991). Rat cerebral astrocytes have been shown to express mainly $ET_B$ type of receptors (Hama et al., 1992) and glial cells also were found to intensely express $ET_B$ receptor mRNA (Pagotto et al., 1995). However, the central administration of a highly selective $ET_B$ receptor agonist, IRL-1620, does not produce any effect on the cardiovascular system, and the systemic and regional circulatory effects of centrally administered ET-1 have been shown to be mediated through the $ET_A$ receptors (Gulati et al., 1995; Rebello et al., 1995).

Intracerebroventricular administration of ET-1 produces a transient rise followed by sustained fall in the mean arterial blood pressure (BP) (Gulati et al., 1996). The pressor effect was accompanied by an increase in renal sympathetic nerve activity and plasma levels of catecholamines and argininevasopressin (Matsumura et al., 1991).

It also has been shown that the effects of central administration of ET-1 are mediated through activation of the sympathetic nervous system because these effects were attenuated by ganglion blockers (Kawano et al., 1989; Matsumura et al., 1991). Intracisternal administration of ET-1 elicited a transient increase in BP, renal sympathetic nerve activity, and phrenic nerve activity. A subsequent fall in BP was accompanied by a decrease in renal sympathetic nerve activity and phrenic nerve activity (Kuwaki et al., 1994). The observation that central ET-1 induced increase in pressor response was suppressed by pretreatment with phenoxybenzamine (Ouchi et al., 1989), further implicates the active participation of sympathetic nervous system in the initial pressor phase.

If central ET-1 is involved in modulating sympathetic activity, then pretreatment with ET receptor antagonist should affect clonidine induced cardiovascular responses. It was found that pretreatment with the $ET_A$ receptor antagonist, BMS-182874, significantly blocked clonidine induced hypotension and bradycardia. BMS-182874 when administered in the lateral cerebral ventricle did not affect BP and HR per se. It becomes clear that, besides cerebral ischemia, other factors, like the sympathetic nervous system, do play a significant role in producing cardiovascular effect following centrally administered ET-1 (Gulati et al., 1997).

It is possible, therefore, to separately potentiate some nonopiate analgesic-induced pharmacological responses, like antipyresis, while other responses, like analgesia, are not affected by an ET antagonist, such as BQ123.

Acetaminophen is one of the most widely used analgesics and antipyretics used for the management of pain and fever in innumerable disease conditions. It has been discovered that using an ET antagonist together with a nonopioid analgesic, like acetaminophen, increases the antipyretic action of the analgesic, without affecting the analgesic action of the analgesic.

Therefore, in accordance with an important feature of the present invention, a nonopioid analgesic is present in a composition, or is administered, with an endothelin antagonist in a weight ratio of analgesic-to-antagonist of about 0.01:1 to about 100:1, and preferably about 0.01:1 to about 10:1. This ratio depends upon the type and identity of nonopioid analgesic and endothelin antagonist being used. The ratio of nonopioid analgesic-to-endothelin antagonist that is administered is dependent upon the particular analgesic and antagonist used, and the severity of the fever being treated. This ratio can be readily determined by a person skilled in the art to achieve the desired antipyretic action.

A nonopioid analgesic utilized in the present invention can be one or more nonopiate analgesic. Specific nonopioid analgesics include, but are not limited to, acetaminophen, phenacetin, ibuprofen, fenoprofen, aspirin, indomethacin, naproxen, oxyphenbutazone, phenylbutazone, allopurinol, cholchicine, carbamazepine, methyl sergide, methotrimeprazine, propoxyphene, probenecid, salsalate, sulfinpyrazone, antipyrine, ethoheptazine, amodiaquine, diflunisal, dihydroergotamine, ergotamine, meclofenamate, mefenamic acid, piroxican, sulindac, tolmetin, and salts, prodrugs, and derivatives, thereof.

An endothelin antagonist utilized in the present invention can be any of the endothelin receptor antagonists known in the art. Endothelin is a potent vasoconstrictor. Endothelin antagonists are used to treat acute heart failure, congestive/chronic heart failure, pulmonary arterial hypertension, pulmonary edema, subarachnoid hemorrhage, chronic obstructive pulmonary disease, myocardial infarction, acute cerebral ischemia, acute coronary syndromes, acute renal failure, post-operative treatment in liver operations, and prostate cancer.

Preferred ET antagonists are antagonists selective for endothelin A ($ET_A$) receptors or are balanced $ET_A$/endothelin B ($ET_B$) antagonists. Such ET antagonists are set forth in Appendices A and B herein. However, endothelin B antagonists and miscellaneous endothelin antagonists, as set forth in Appendices C and D herein, also can be used in a composition or method of the present invention. Additional useful endothelin antagonists can be found in U.S. patent application Publication No. 2002/0,082,285 A1, incorporated herein by reference.

Specific examples of endothelin antagonists useful in the present invention include, but are not limited to, atrasentan, tezosentan, bosentan, darnsentan, sitaxsentan, enrasentan, BMS-207940 (Bristol-Myers Squibb), BMS-193884, BMS-182874, J-104132 (Banyu Pharmaceutical), VML 588/Ro 61-1790 (Vanguard Medica), T-0115 (Tanabe Seiyaku), TAK-044 (Takeda), BQ-788, BQ123, YM-598, LU 135252, PD 145065, A-127722, ABT-627, A-192621, A-182086, TBC3711, BSF208075, S-0139, TBC2576, TBC3214, PD156707, PD180988, ABT-546, ABT-627, Z1611, RPR118031A, SB247083, SB217242, S-Lu302872, TPC10950, and SB209670.

BQ123 is a specific endothelin A antagonist, and is the sodium salt of cyclo (-D-Trp-D-Asp-Pro-D-Val-Leu-). BQ-788 is a specific endothelin B antagonist, and is the sodium salt of N-cis-2,6-dimethylpiperidinocarbonyl-L-gamma-methylleucyl-D-1-methoxycarbonyl triptophanyl-DNle (see *Proc. Natl. Acad. Sci. USA*, 91, pp. 4892-4896 (1994)).

In addition to a conventional endothelin antagonist, a compound that inhibits the formation of endogenous endothelin also can be used as the endothelin antagonist in the present invention. Such compounds are useful because they prevent endothelin formation, and, therefore, decrease the activity of endothelin receptors. One class of such compounds is the endothelin converting enzyme (ECE) inhibitors.

Useful ECE inhibitors include, but are not limited to, CGS34225 (i.e., N-((1-((2-(S)-(acetyl-thio)-1-oxopentyl)-amino)-1-cyclopentyl)-carbonyl-S-4-phenylphenyl-alanine methyl ester) and phosphoramidon (i.e., N-(a-rhamnopyranosyloxyhydroxyphosphinyl)-Leu-Trp).

It has been found that the antipyretic action of a nonopioid analgesic, like acetaminophen, can be potentiated by an endothelin (ET) receptor antagonist, like BQ123, or an ECE without affecting the analgesic action of the nonopioid analgesic and independent of the underlying cause of the fever. The following tests were conducted to illustrate the antipyretic potentiating effects of an endothelin antagonist on a nonopioid analgesic administered to a mammal, including humans.

Male Swiss-Webster mice weighing 25 to 30 grams (Harlan, Indianapolis, Ind.) were housed four per cage in a room having a controlled ambient temperature ($23\pm1°$ C.), humidity ($50\pm10\%$), and twelve-hour light/dark cycle (6:00 a.m. to 6:00 p.m.). Food and water were available ad libitum. The experiments were-performed after the mice were acclimated to this environment for at least four days.

Acetaminophen was purchased from Sigma Chemical Co., St. Louis, Mo. BQ123 was purchased from American Peptide Company Inc., Sunnyvale, Calif. BQ123 was dissolved in sterile saline and injected intracerebroventricularly (i.c.v.).

Schedule of Drug Administration

For i.c.v. administration of the endothelin antagonist BQ123, a mouse was grasped firmly by the loose skin behind the head and the skin was pulled taut. The site of injection was 2 mm from either side of the midline drawn through the anterior base of the ears. A 27 gauge sterile hypodermic needle attached to a 10 μL sterile Hamilton syringe was inserted perpendicularly through the skull into the brain, and vehicle (sterile saline) or BQ123 was delivered to the ventricle of the mouse brain (see T. J. Haley et al., *Brit. J. Pharmacol.*, 12(12), (1957)). BQ123 (3 μg) or vehicle was administered i.c.v. and volume of drug injection was 5 μL. Vehicle or BQ123 pretreatment was performed 30 minutes prior to administration of acetaminophen (300 mg/kg s.c.).

The mice were divided into the following four groups (N=5 in each group): group 1 (P+V) received vehicle (V) (saline 5 μl, i.c.v.) and placebo (P) (vehicle 100 μl/kg, s.c.); group 2 (P+BQ) received BQ123 (BQ) (3 μg. i.c.v. in a volume of 5 μl of saline) and placebo (P) (vehicle 100 μl/kg, s.c.); group 3 (A+V) received vehicle (V) (saline 5 μl, i.c.v.) and acetaminophen (A) (300 mg/kg, s.c. in a volume of 100 μl/kg); and group 4 (A+BQ) received BQ123 (BQ) (3 μg, i.c.v. in a volume of 5 μl) and acetaminophen (A) (300 mg/kg, s.c. in a volume of 100 μl/kg). Vehicle or BQ123 pretreatment was performed 30 minutes prior to administration of acetaminophen (FIG. 1).

Measurement of Tail-Flick Latency

An analgesic response was determined by the tail flick method (C. Advocat et al., *Brain Ref.*, 55(2), pp. 251-258 (1991); H. N. Bhargava, *General Pharmacology*, 28(1), pp. 61-64 (1997)). The tail flick latencies to thermal stimulation (focused light) were determined before and 30, 60, 90, 120, 180, 210, 240, 270, 300, and 360 minutes after injection of acetaminophen. The basal tail flick latency was about 2 seconds. A thermal stimulation cutoff time of 10 seconds was used to prevent damage to the tail of the animal. The analgesic response in each mouse was expressed as mean±SEM.

Measurement of Body Temperature

The change in body temperature in response to acetaminophen (300 mg/kg) was determined (Bhargava, 1997). The colonic temperature of each mouse was recorded before and at various times after the injection of acetaminophen over a period of 360 minutes using a telethermometer. Body temperature data was expressed as mean±SEM.

Statistics

All data are presented as mean values±SEM. Student t-test and paired t-test were used. Differences within and between groups were tested using ANOVA. A level of P<0.05 was considered significant.

RESULTS

Effect on Body Weight

The body weight of all mice was measured, and no change in body weight between various groups of mice was observed (FIG. 2). Body weight was measured before administration of any drug and at the end of the experiment (i.e., 7 hours after the administration of acetaminophen). Test results clearly showed that all four groups of mice were essentially equal in their response to change in body weight, and that neither acetaminophen nor BQ123 produced any acute effect on body weight.

Effect on Body Temperature

The control test (i.e., administration of placebo and vehicle) did not produce any change in the body temperature of the mice. BQ123 administration also did not produce any significant change in body temperature. Acetaminophen administration, however, produced a significant hypothermia in mice. The hypothermia lasted for about three hours after the administration of acetaminophen. The hypothermic effect of acetaminophen was significantly potentiated by BQ123 administration. The hypothermic effect of acetaminophen not only was significantly greater in BQ123 pretreated mice, but lasted for more than six hours (FIGS. 3, 4, and 5). This is a very significant result because the endothelin antagonist BQ123 markedly potentiated the hypothermic response to acetaminophen, and the acetaminophen-induced analgesic effect was not affected (FIG. 6).

Effect on Analgesia

The control (i.e., placebo and vehicle) group of mice exhibited tail flick latencies of about 2 seconds. BQ123 administration did not produce any significant effect on tail flick latency of the mice. Acetaminophen administration (300 mg/kg, s.c.) produced significant analgesia in mice, and the tail flick latencies reached more than 10 seconds. A significant increase in tail flick latencies was observed for three hours after the administration of acetaminophen. This analgesic effect of acetaminophen was not affected by BQ123 administration (FIG. 6).

The data presented herein clearly show that BQ123 significantly potentiates the hypothermic effect of acetaminophen. The duration of hypothermia induced by acetaminophen also was increased following BQ123 pretreatment. The analgesic effect of acetaminophen was not affected by BQ123.

Fever is one of the most common symptoms or manifestations associated with numerous conditions and diseases. Acetaminophen and other nonopioid analgesics are the most commonly used drugs to control fever. The present invention, therefore, enhances the antipyretic action of a nonopioid analgesic independent of the underlying cause of the fever.

The present composition and method do not treat the underlying disease or condition causing the fever, except for conditions and diseases treatable using an endothelin antagonist or nonopioid antagonist. Therefore, the present invention, which is directed to a novel method and composition to potentiate the antipyretic action of a nonopioid analgesic, can be useful as a primary treatment or an adjunct treatment of any disease or condition that causes fever.

The present invention, therefore, is useful as an improved treatment of a disease or condition treatable with an endothelin antagonist (a) by achieving the curative effects of the endothelin antagonist and (b) by significantly improving the antipyretic action of a nonopioid analgesic administered to reduce a fever associated with the disease or condition.

For example, one disease or condition of particular interest is stroke. Fever has been correlated to serious problems and a poor prognosis for individuals who suffered an acute stroke. In particular, mild alterations in body temperature have pronounced effects on ischemic cell injury and recovery from a stroke. Elevated core body temperature (CBT), even if mild, exacerbates neuronal injury and can adversely affect recovery prognosis, whereas hypothermia is potentially neuroprotective.

It is known that early administration of acetaminophen (3900 mg/d) to afebrile patients suffering from acute stroke can provide a small reduction in CBT. Acetaminophen also can promote moderate hypothermia (<36.5° C.) or prevent hypothermia (>37.5° C.) (see S. E. Kasner, *Stroke*, 33(1), pp. 130-134 (2002)). In another study, forty-two, normothermic patients suffering from acute ischemic stroke were randomized within 24 hours from symptom onset to receive either 4000 mg acetaminophen (n=20), or a matched placebo (n=22), daily. A fever of greater than 37.5° C. occurred in 36.4% of patients in the placebo group, compared to 5.0% in the acetaminophen group (Fisher's exact test, p=0.014).

Prophylactic antipyretic treatment using acetaminophen, therefore, can be effective in the treatment of stroke by reducing or preventing fever after acute ischemic stroke. In particular, H. C. Koenneoke et al., *Neurology*, 57(12), pp. 2301-2302 (2002), reported that seventy-five patients having acute ischemic stroke confined to the anterior circulation were randomized for treatment with either 500 mg (low dose) or 1000 mg (high dose) acetaminophen or with placebo, administered as suppositories six times daily over five days. Treatment with a daily dose of 6000 mg acetaminophen resulted in a small, but potentially beneficial, decrease in body temperature shortly after ischemic stroke, even in normothermic and subfebrile patients (D. W. Dippel et al., *Stroke*, 32(7), pp. 1607-1612 (2001)).

In summary, the antipyretic action of the present composition and method in the treatment of stroke is of particular interest in the present invention because: (a) endothelin antagonists are known as useful drugs in the treatment of stroke;

(b) fever is associated with a poor prognosis in acute stroke because elevated core body temperature (CBT), even if mild, can exacerbate neuronal injury and worsen prognosis, whereas hypothermia is potentially neuroprotective; and (c) acetaminophen presently is being promoted for use shortly after stroke to reduce the body temperature and thereby improve the long-term prognosis for stroke patients.

Therefore, a combination treatment using BQ123 (or other endothelin antagonist) and acetaminophen (or other nonopioid analgesic) is useful both in the treatment of stroke and in palliating or eliminating the adverse effects of fever associated with a stroke. This combination synergistically reduces CBT more than acetaminophen alone, while an endothelin antagonist, like BQ123, provides an additional advantage by treating stroke and helping to reduce damage to the brain. The combination of an endothelin antagonist and nonopioid analgesic, therefore, has a dual effect, i.e., treatment of stroke and a synergistic antipyretic action.

In addition, a combination treatment using an endothelin antagonist, e.g., BQ123, and a nonopioid analgesic, e.g., aspirin, can be used to prevent stroke and other cardiovascular disorders, such as myocardial infarction. Administration of aspirin is well-known as a preventative treatment for stroke and heart attack. By combining the aspirin treatment with an endothelin antagonist, the antipyretic action of aspirin is realized, together with the potentiating effect of the endothelin antagonist and the antiplatelet actions of aspirin and other nonopioid analgesics.

In addition, the present method and composition can be used whenever a fever is associated with a condition or disease treatable with an endothelin antagonist-type of drug. Examples of such fevers are those in patients suffering from hypertension, pulmonary hypertension, congestive heart failure, and postoperative management of fever. A method and composition of the present invention also can significantly improve pyrexia associated with management of neuroleptic malignant syndrome, neoplastic fever, endotoxemia, and related conditions and diseases.

It also is theorized, but not relied upon, that an endothelin antagonist, like BQ123, acts on a yet unidentified receptor or mechanism. Therefore, any compound related to such unknown receptor or mechanism is useful in potentiating the antipyretic action of a nonopioid analgesic in accordance with the present invention.

The test results clearly demonstrate that endothelin antagonists, like BQ123, can potentiate nonopioid analgesia-induced antipyresis without affecting analgesia. This is an important clinical finding because endothelin antagonists have minimal cardiovascular effects in normal healthy individuals. Endothelin antagonists combined with a nonopioid analgesic, therefore, can be used to potentiate the antipyretic action of the analgesic without affecting the pharmacological action, i.e., analgesia, of the nonopioid analgesic.

These findings show that when combined with an endothelin antagonist, nonopiate analgesics produce significant antipyretic action, without adversely affecting analgesic activity. The data shows that it is possible to separately potentiate some pharmacological responses, like enhanced antipyresis, while other responses, like analgesia, are not affected by endothelin antagonist administration. The above tests and data further show that a combination of a nonopioid analgesic and an endothelin antagonist can be administered to mammals in methods of treating pain and providing an enhanced antipyretic action.

The nonopioid analgesic and endothelin antagonist can be formulated in suitable excipients for oral administration, or for parenteral administration. Such excipients are well known in the art. The active agents typically are present in such a composition in an amount of about 0.1% to about 75% by weight, either alone or in combination.

Pharmaceutical compositions containing the active agents, i.e., nonopioid analgesic and endothelin antagonist, of the present invention are suitable for administration to humans or other mammals. Typically, the pharmaceutical compositions are sterile, and contain no toxic, carcinogenic, or mutagenic compound which would cause an adverse reaction when administered.

The method of the present invention can be accomplished using the active agents as described above, or as a physiologically acceptable salt, derivative, prodrug, or solvate thereof. The active agents, or a form thereof, can be administered as the neat compound, or as a pharmaceutical composition containing either or both entities. Administration of the pharmaceutical composition, or individual active ingredients, can be performed before, during, or after the onset of fever.

The active agents can be administered by any suitable route, for example by oral, buccal, inhalation, sublingual, rectal, vaginal, intracisternal through lumbar puncture, transurethral, nasal, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

The pharmaceutical compositions include those wherein the active ingredients are administered in an effective amount to achieve their intended purpose. More specifically, a "therapeutically effective amount" means an amount effective to prevent development of, to eliminate, or to reduce fever. Determination of a therapeutically effective amount is well within the capability of those skilled in the art, especially in light of the detailed disclosure provided herein.

A "therapeutically effective dose" refers to that amount of the active agents that results in achieving the desired effect. Toxicity and therapeutic efficacy of such active agents can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred The data obtained from such data can be used in formulating a range of dosage for use in humans. The dosage of the active agents preferably lies within a range of circulating concentrations that include the $ED_{50}$ with little or no toxicity. The dosage can vary within this range depending upon the dosage form employed, and the route of administration utilized.

The exact formulation, route of administration, and dosage is determined by an individual physician in view of the patient's condition. Dosage amount and interval can be adjusted individually to provide levels of the active agents that are sufficient to maintain therapeutic or prophylactic effects.

The amount of pharmaceutical composition administered is dependent on the subject being treated, on the subject's weight, the severity of the affliction, the manner of administration, and the judgment of the prescribing physician.

Specifically, for administration to a human in the curative or prophylactic treatment of pain, oral dosages of a nonopioid analgesic and endothelin antagonist, individually generally are about 10 to about 200 mg daily for an average adult patient (70 kg), typically divided into two to three doses per day. Thus, for a typical adult patient, individual tablets or capsules contain about 0.1 to about 200 mg nonopioid analgesic and about 0.1 to about 50 mg endothelin antagonist, in a suitable pharmaceutically acceptable vehicle or carrier, for administration in single or multiple doses, once or several times per day. Dosages for intravenous, buccal, or sublingual administration typically are about 0.1 to about 10 mg/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

The active agents of the present invention can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active agents into preparations which can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the active agents are administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% of an active agent of the present invention, and preferably from about 25% to about 90% compound of the present invention. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.5% to about 90% by weight of active agents, and preferably about 1% to about 50% of an active agents.

When a therapeutically effective amount of the active agents is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

Suitable active agents can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the active agents with a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The active agents can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of the active agents can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The active agents also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the active agents can be formulated with suitable polymeric or hydrophobic materials (for example, as an emulsion in an acceptable oil) or ion exchange resins, or as sparingly soluble derivatives, for example, as a sparingly soluble salt.

In particular, the active agents can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, intrathecally, intracisternally, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, the active ingredients are administered as a suitably acceptable formulation in accordance with normal veterinary practice. The veterinarian can readily determine the dosing regimen and route of administration that is most appropriate for a particular animal.

As stated above, acetaminophen is one of the most commonly used analgesics, and is widely used for pain and fever management in several disease conditions, including stroke. It has been discovered that using an endothelin antagonist together with a nonopioid analgesic, like acetaminophen, potentiates the antipyretic action of the analgesic, but does not adversely affect the analgesic action of the analgesic.

REFERENCES

A. Gulati et al., *Life Sci*, 58(5):437-45 (1996).

A. Gulati et al., *Life Sci*, 51(22):1715-24 (1992).

A. Gulati et al., *Am J Physiol*, 273(3 Pt 2):H1177-86 (1997).

A. Gulati et al., *J Cardiovasc Pharmacol*, 26(Suppl 3):S244-6 (1995).

H. Hama et al., *Biochem Biophys Res Commun*, 186(1):355-62 (1992).

K. A. Hickey et al., *Am J Physiol*, 248(5 Pt 1):C550-6 (1985).

Himmelsbach, *Fed Proc*, 2:201-203 (1943).

M. Ihara et al., *Life Sci*, 50(4):247-55 (1992).

Y. Kawano et al., *J Hypertens Suppl* 7(6):S22-3 (1989).

T. Kuwaki et al., *Jpn J Physiol*, 44(1):1-18 (1994).

M. W. MacCumber et al., *Proc Natl Acad Sci USA*, 87(6): 2359-63 (1990).

K. Matsumura et al., *Hypertension*, 17(6 Pt 2):1192-6 (1991).

Y. Ouchi et al., *Am J Physiol*, 256(6 Pt 2):H1747-51 (1989).

U. Pagotto et al., *J Cardiovasc Pharmacol*, 26(Suppl 3):S104-6 (1995).

S. Rebello et al., *Brain Res*, 676(1):141-50 (1995).

E. E. Reynolds et al., *Biochem Biophys Res Commun*, 160(2):868-73 (1989).

P. D. Stein et al., *J Med Chem*, 37(3):329-31 (1994).

M. Yanagisawa et al., *J. Hypertens Suppl* 6(4):S188-91 (1988).

Modifications and variations of the invention as hereinbefore set forth can be made without departing from the spirit and scope thereof, and, therefore, only such limitations should be imposed as are indicated by the appended claims.

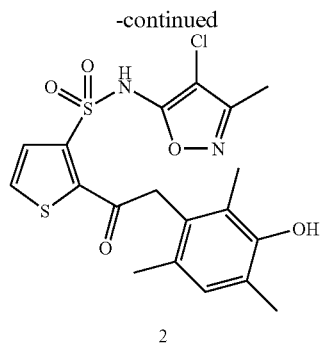

1
sitaxsentan

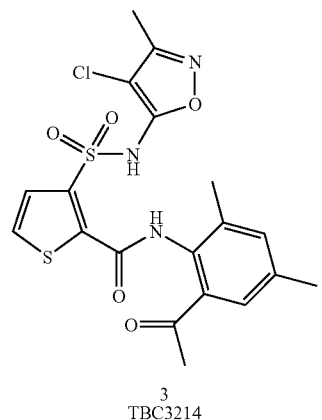

2
TBC2576

3
TBC3214

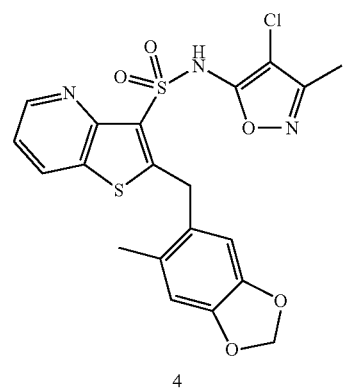

4

5

-continued
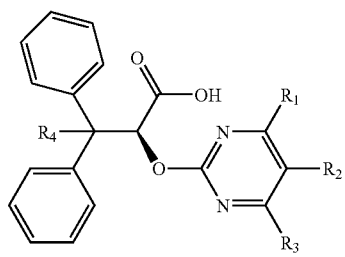
6  $R_1 = R_3 = R_4 = CH_3$, $R_2 = H$
7  $R_1 = R_3 = R_4 = OCH_3$, $R_2 = F$
8  $R_1 = OCH_3$, $R_2 = H$, $R_3 = CH_3$, $R_4 = $ —$OCH_2CON(CH_3)C_6H_5$
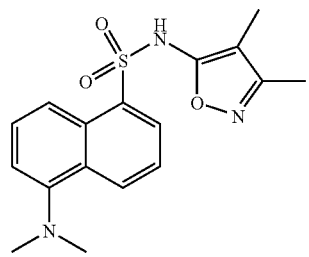
9
BMS 182, 874
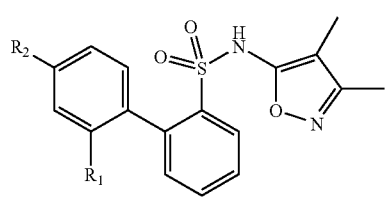
10  $R_1 = CH_2OH$, $R_2 = H$
11  $R_1 = H$, $R_2 = $ 2-oxazolyl
12  $R_1 = H$, $R_2 = $ 2-pyrimidinyl
13  $R_1 = H$, $R_2 = $ 4-methoxyethoxymethyl-4-oxo-1, 2, 4-triazol-2-yl
14  $R_1 = H$, $R_2 = $ 1, 3-diazo-2-butyl-4-oxospiro (4, 4)-1-nonen-3-ylmethyl
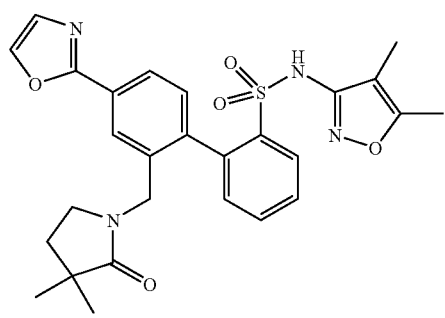
15
-continued
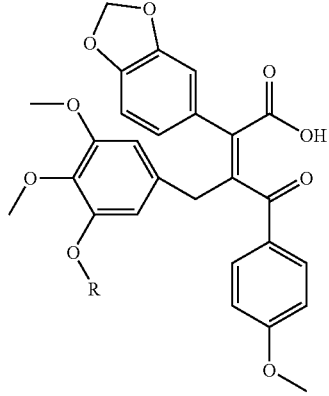
16  R = $CH_3$  (PD156707)
17  R = $CH_2CH_2SO_3H$
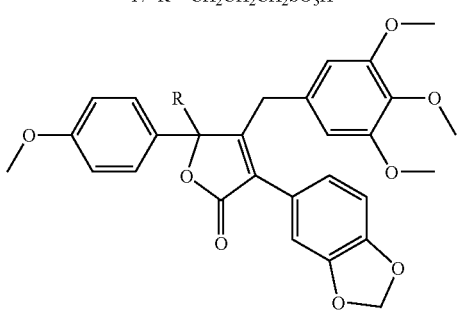
18  R = $OCH_2CH_2CH_2SO_3H$
19  R = $OCONHCH_2CO_2C_2H_5$
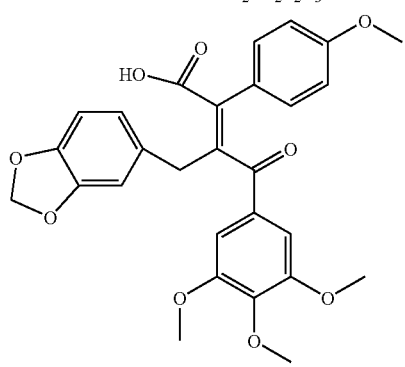
20
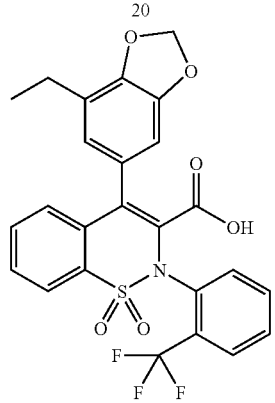
21
PD180988

-continued
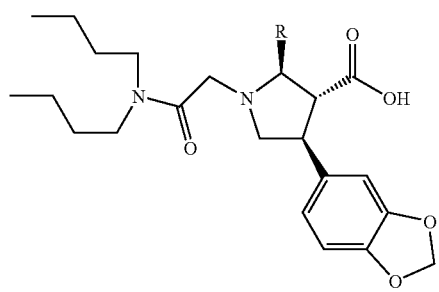
22 R = C6H4-4-OCH3 (ABT-627)
23 R = CH2CH2-2-pyridyl
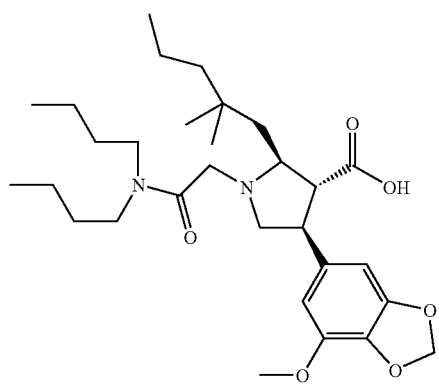
24
ABT-546
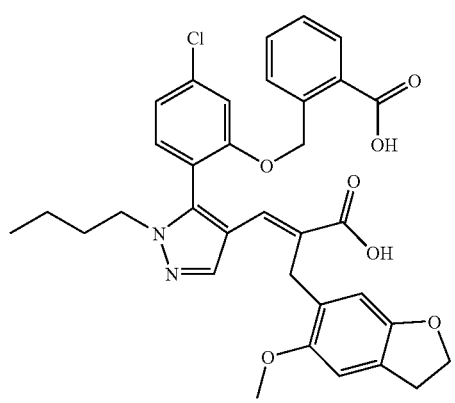
25
SB247083
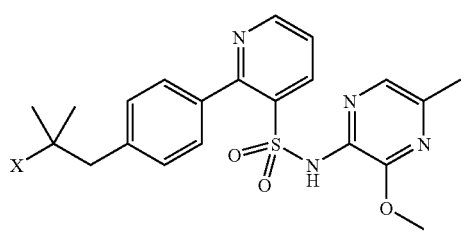
26 X = CO2H (Z1611)
27 X = H
-continued
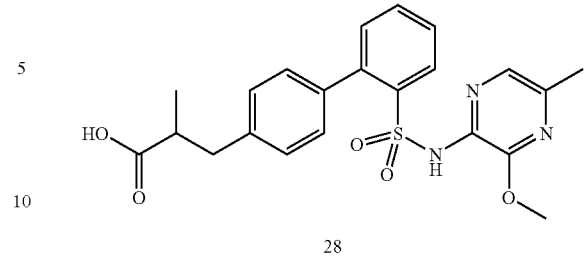
28
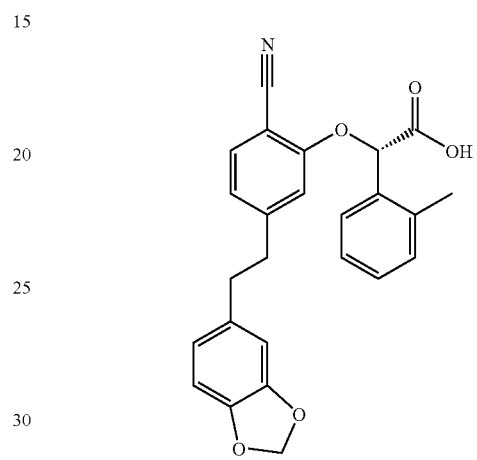
29
RPR118031A
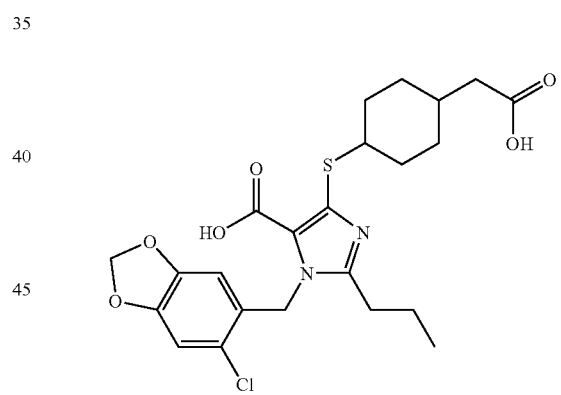
30
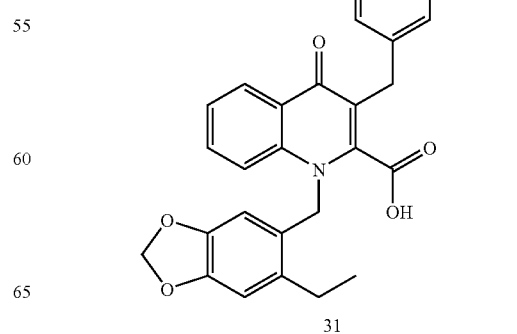
31

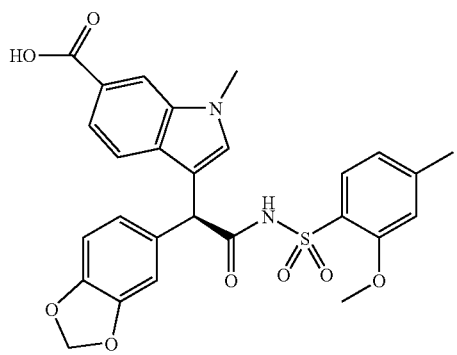
32
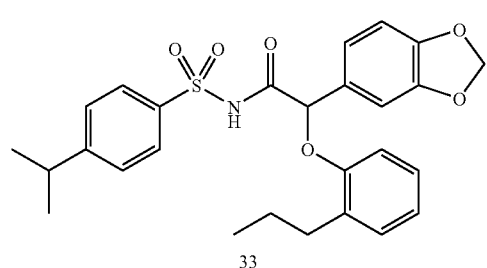
33
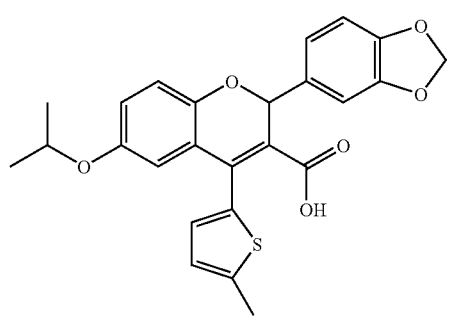
34
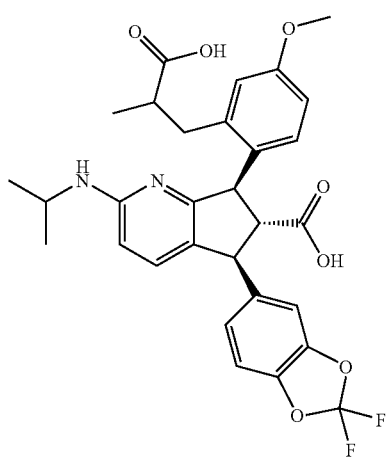
35
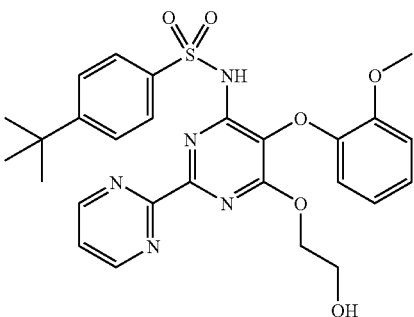
46
bosentan
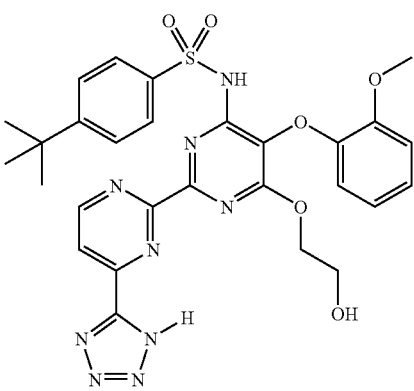
47
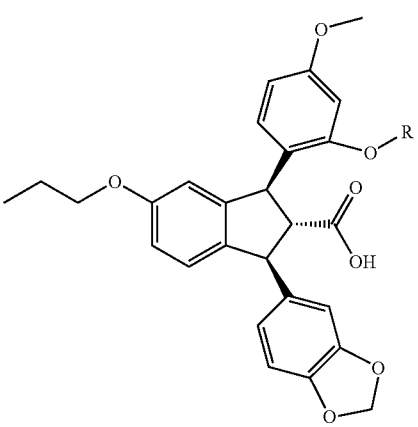
48  R = CH$_2$CO$_2$H  SB209670
49  R = CH$_2$CH$_2$OH  SB217242

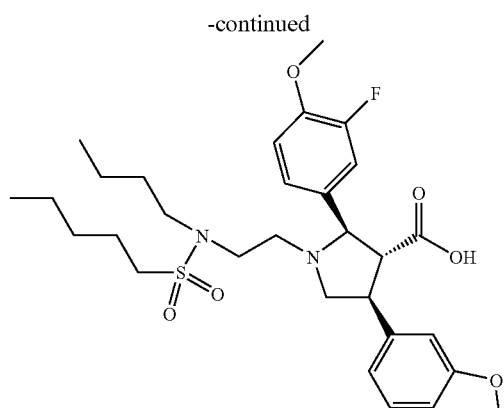
50
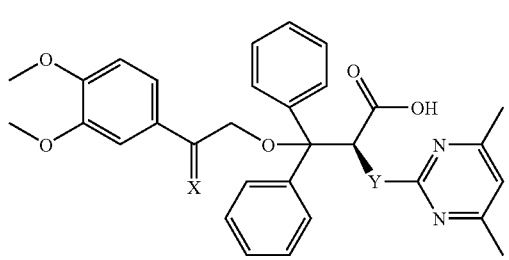
51 X = H₂, Y = CH₂ S-LU 302872
52 X = O, Y = O
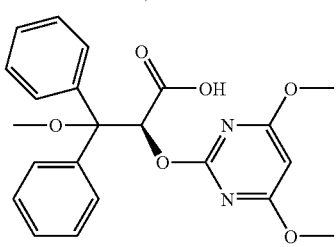
53
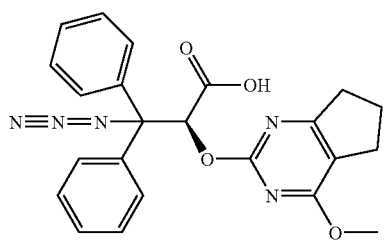
54
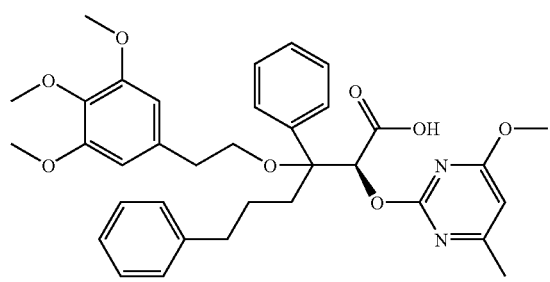
55
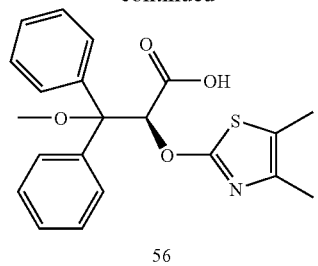
56
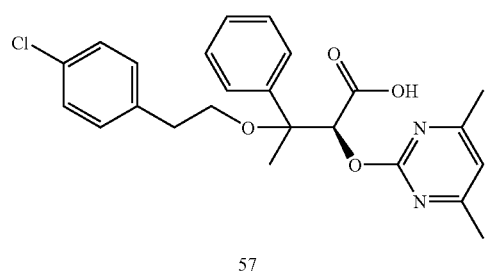
57
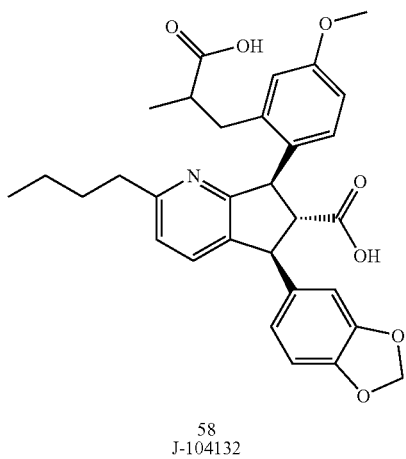
58
J-104132
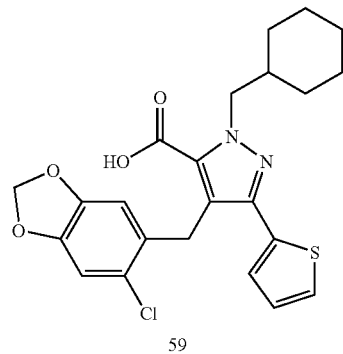
59

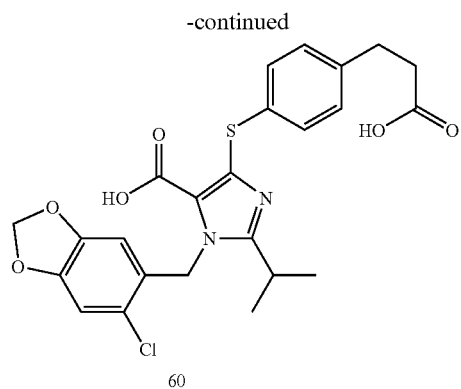
60
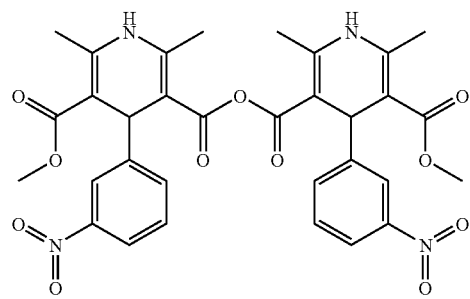
61
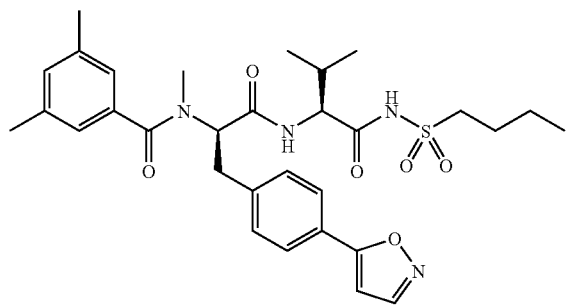
62
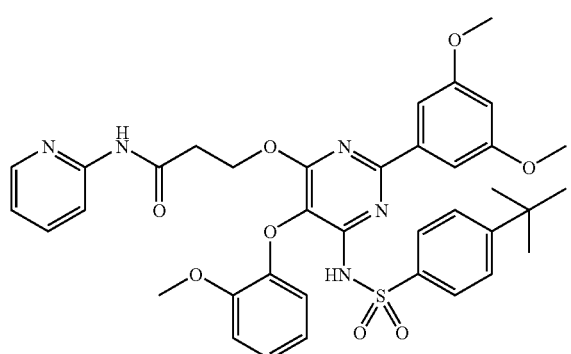
63
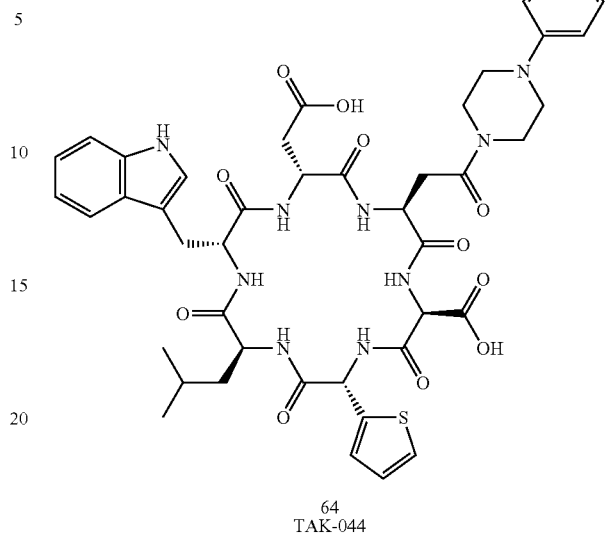
64
TAK-044
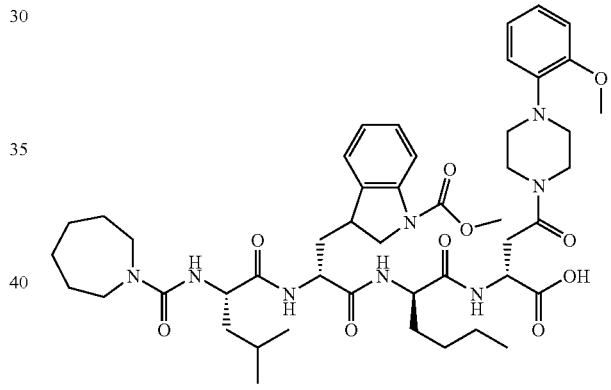
65
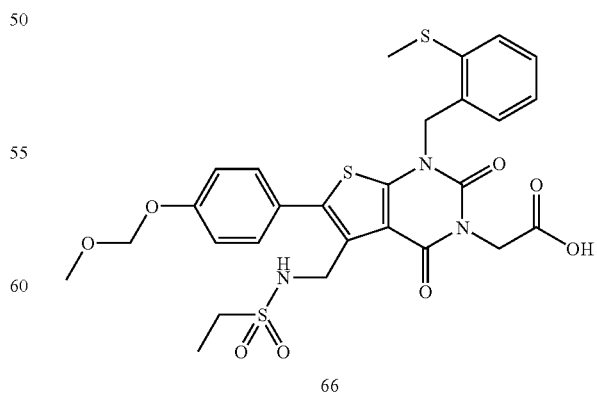
66

-continued
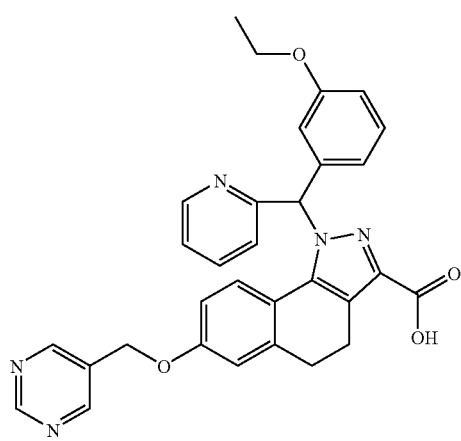
67
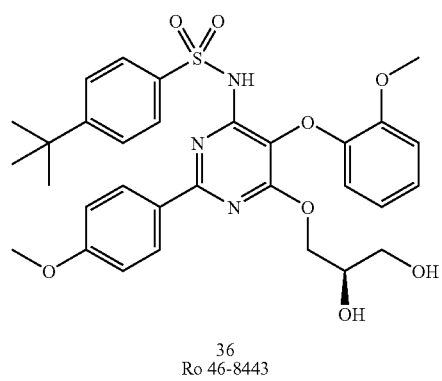
36
Ro 46-8443
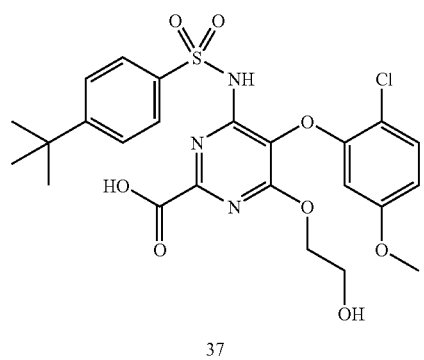
37
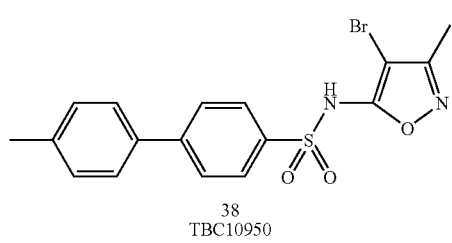
38
TBC10950
-continued
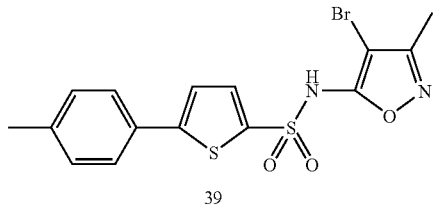
39
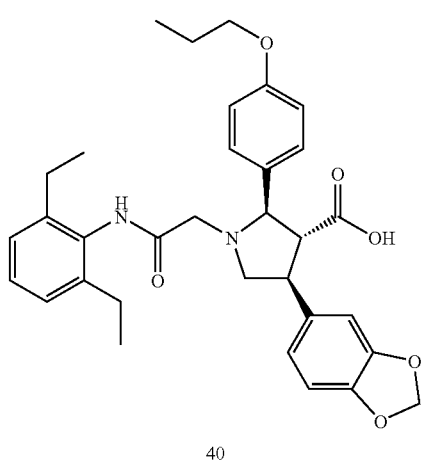
40
A192621
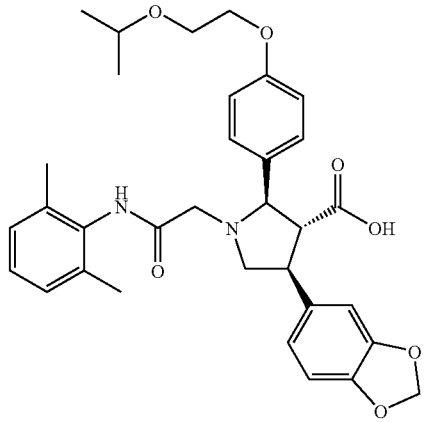
41
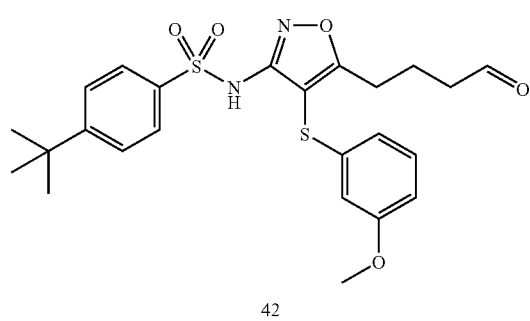
42

-continued
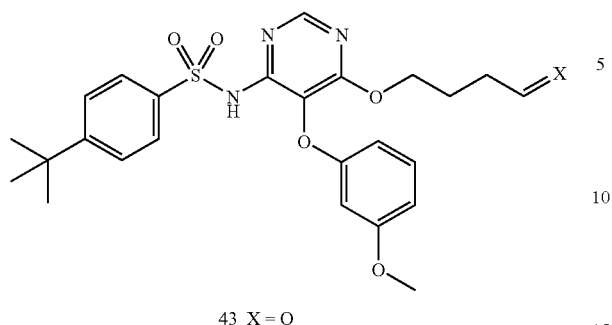
43 X = O
44 X = NNHCO-3-pyridyl
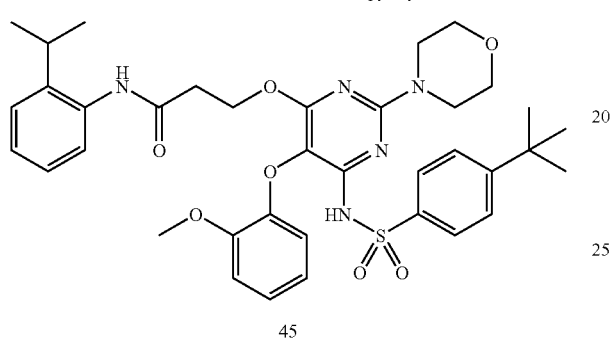
45
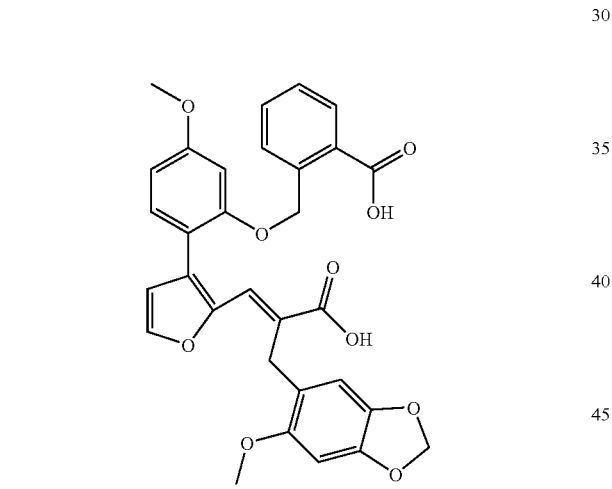
68
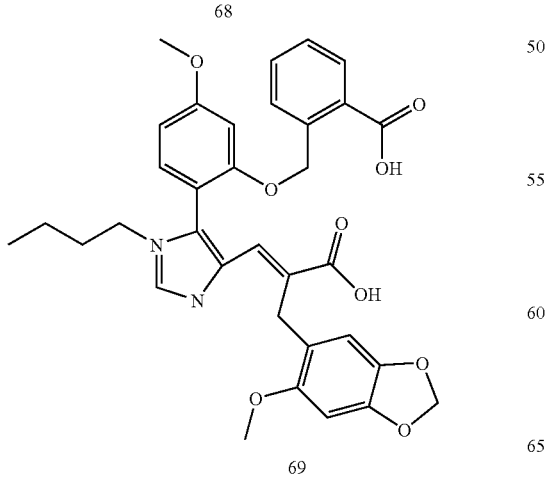
69
-continued
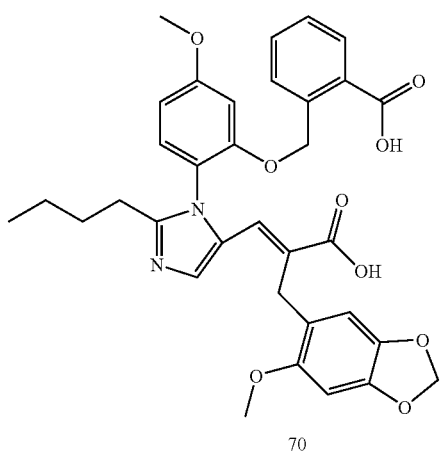
70
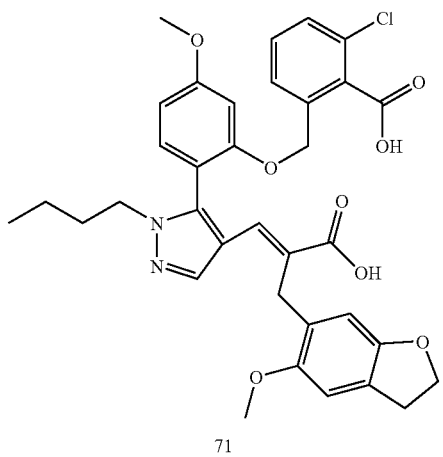
71
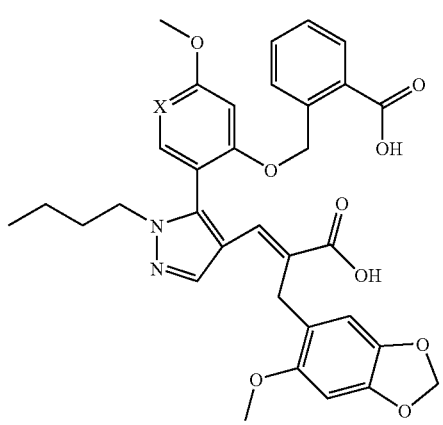
72 X = C
73 X = N -continued
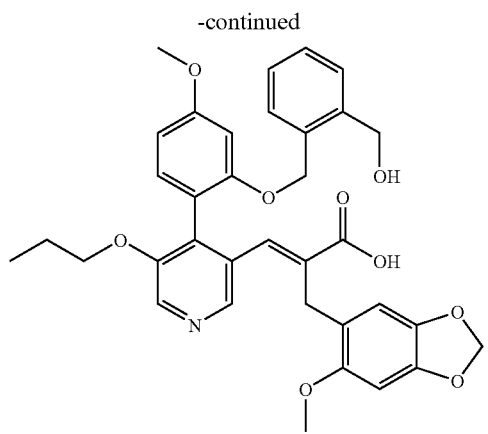
74
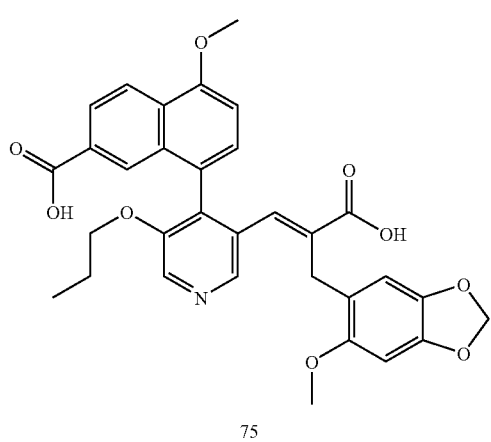
75
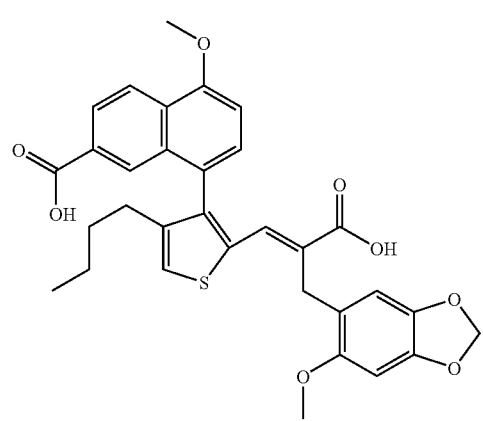
76
-continued
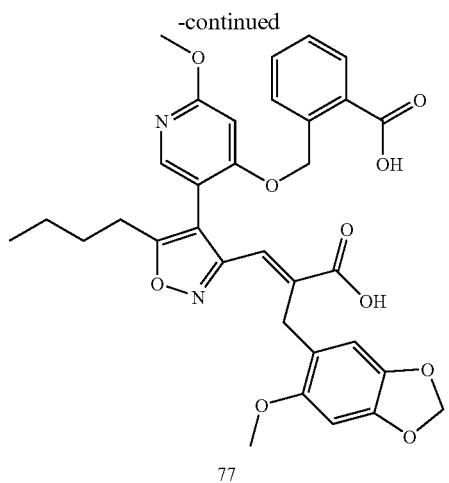
77
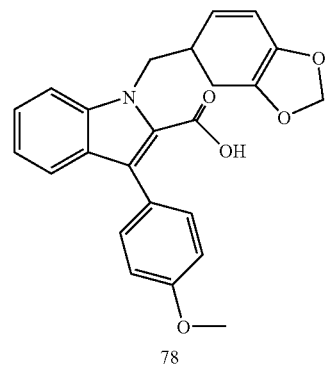
78
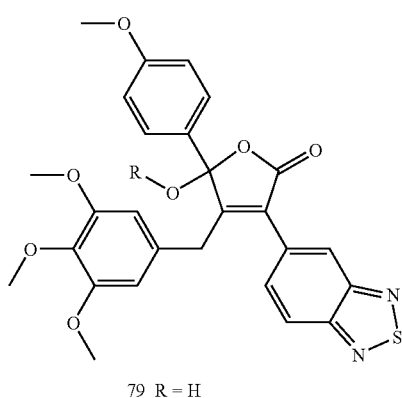
79  R = H
80  R = CONHCH$_2$CO$_2$C$_2$H$_5$
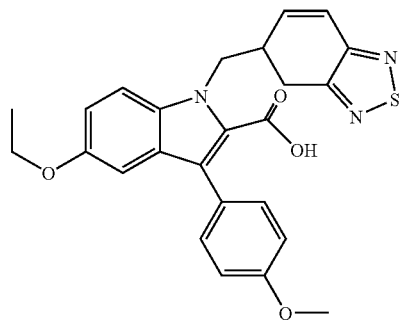
81

-continued
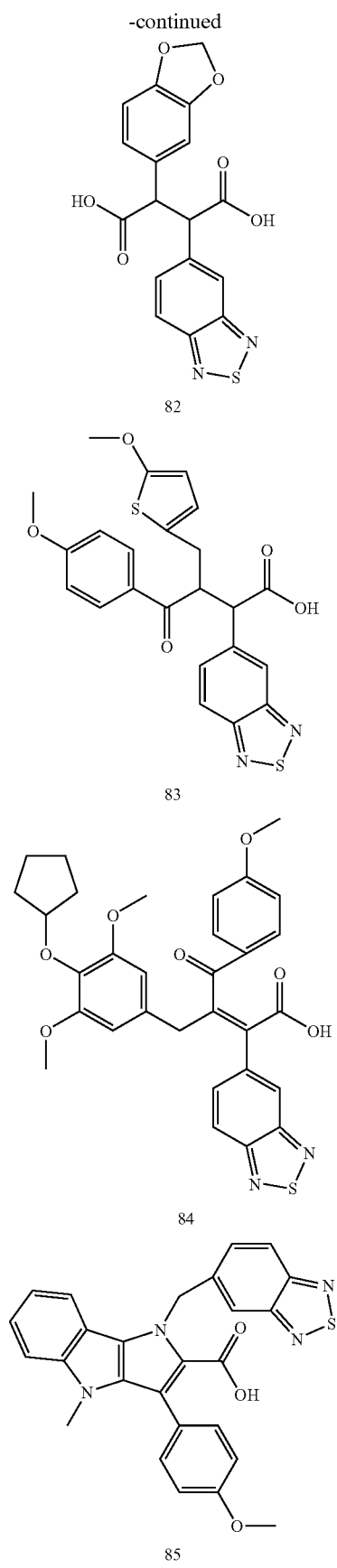
82
83
84
85
-continued
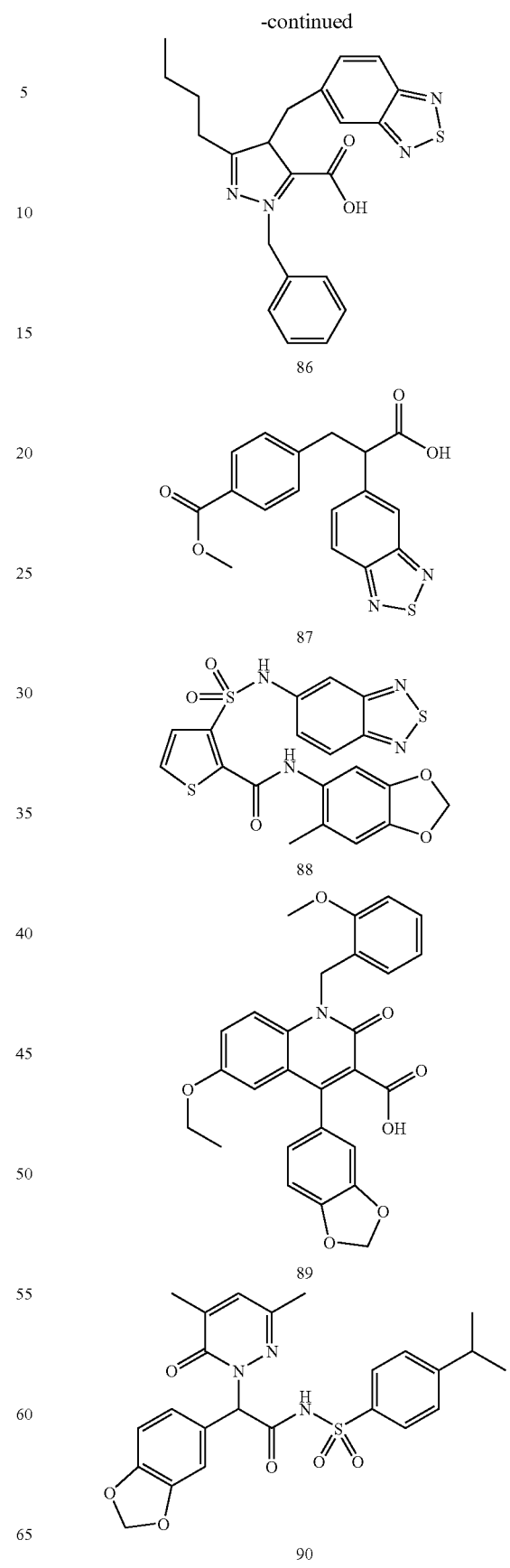
86
87
88
89
90

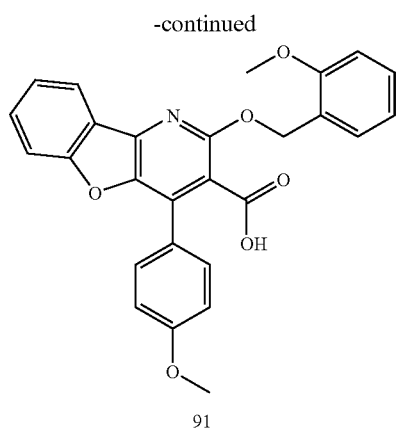
91
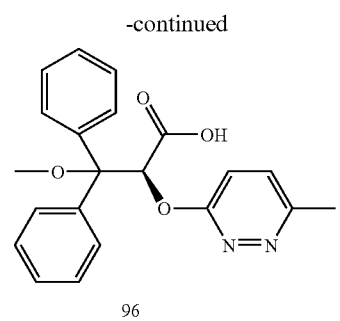
96
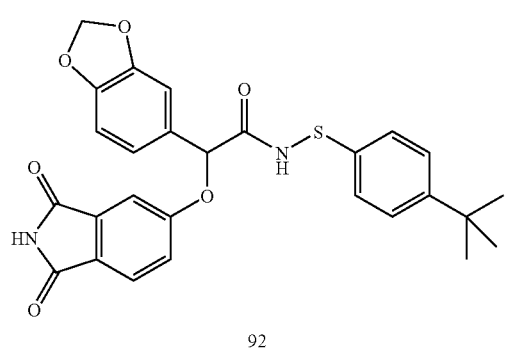
92
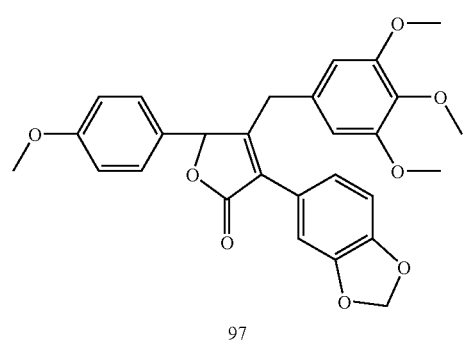
97
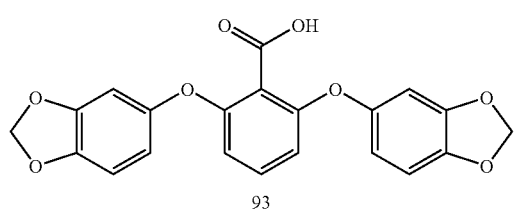
93
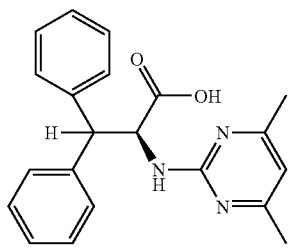
94
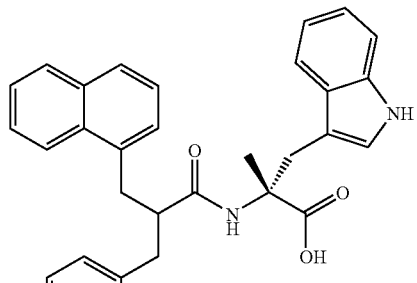
98
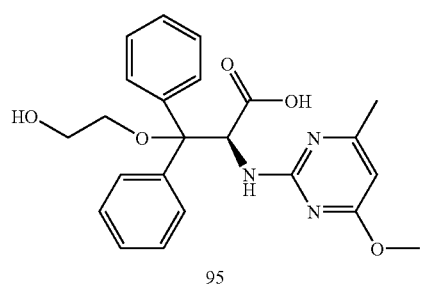
95
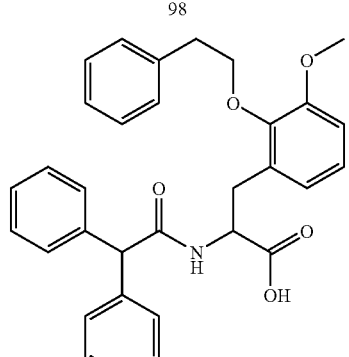
99

-continued
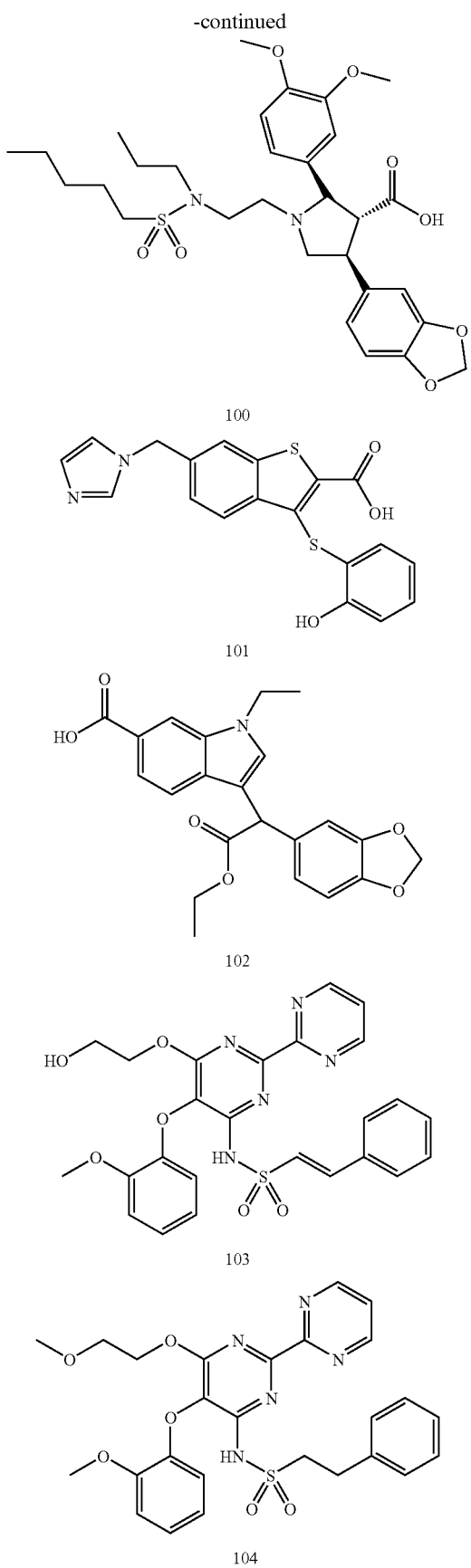
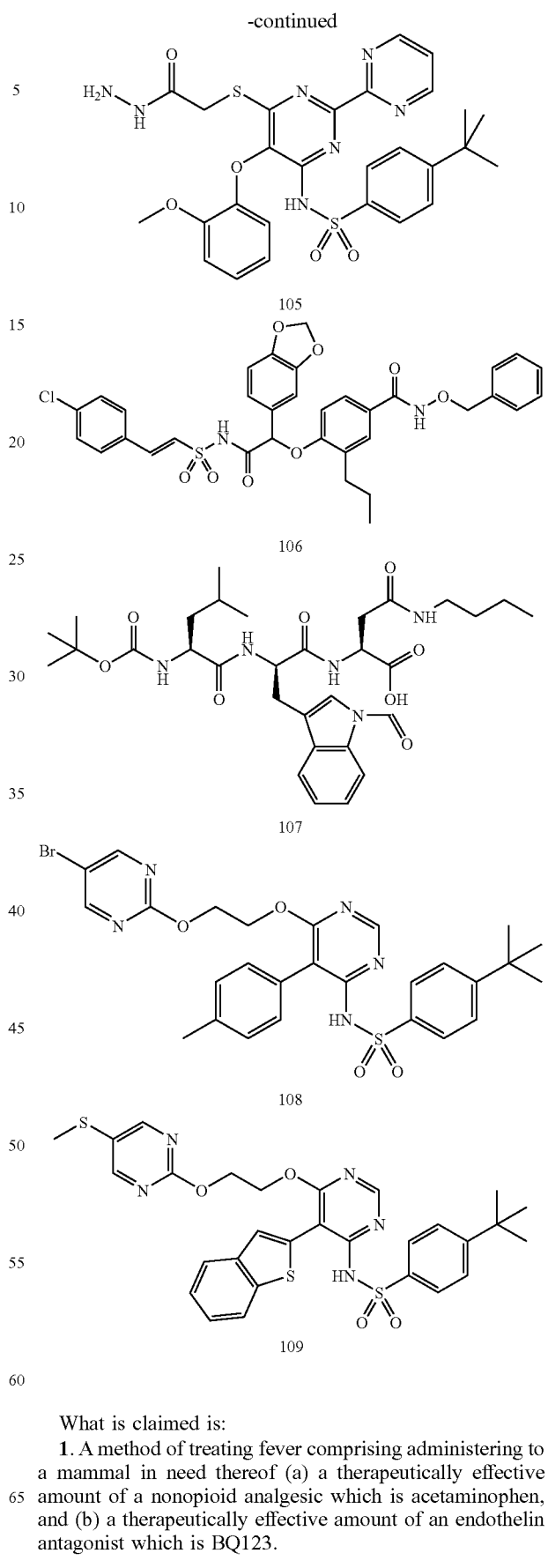
What is claimed is:
1. A method of treating fever comprising administering to a mammal in need thereof (a) a therapeutically effective amount of a nonopioid analgesic which is acetaminophen, and (b) a therapeutically effective amount of an endothelin antagonist which is BQ123.

2. The method of claim 1 wherein the nonopioid analgesic and endothelin antagonist are administered simultaneously.

3. The method of claim 2 wherein the nonopioid analgesic and endothelin antagonist are administered from a single composition.

4. The method of claim 2 wherein the nonopioid analgesic and endothelin antagonist are administered from separate compositions.

5. The method of claim 1 wherein the nonopioid analgesic and endothelin antagonist are administered sequentially.

6. The method of claim 5 wherein the nonopioid analgesic is administered prior to the endothelin antagonist.

7. The method of claim 5 wherein the endothelin antagonist is administered prior to the nonopioid analgesic.

8. The method of claim 1 wherein analgesic properties of the nonopioid analgesic are unaffected.

9. The method of claim 1 wherein the mammal is a human.

10. The method of claim 1 wherein treating the fever comprises reducing severity of the fever.

11. The method of claim 10 wherein the fever is reduced at least 1.5 times longer than a treatment utilizing the nonopioid analgesic alone.

* * * * *